(12) United States Patent
Devdas et al.

(10) Patent No.: US 10,607,469 B2
(45) Date of Patent: Mar. 31, 2020

(54) METHODS FOR DETECTING AND HANDLING FALL AND PERIMETER BREACH EVENTS FOR RESIDENTS OF AN ASSISTED LIVING FACILITY

(71) Applicant: PHILIPS NORTH AMERICA LLC, Andover, MA (US)

(72) Inventors: Vikram Devdas, Vancouver (CA); Dan Erichsen, Burnaby (CA); Kenneth Wagner, Ottawa (CA); Richard Heaton, San Jose, CA (US)

(73) Assignee: PHILIPS NORTH AMERICA LLCMA (US)

( * ) Notice: Subject to any disclaimer, the term of this patent is extended or adjusted under 35 U.S.C. 154(b) by 0 days.

(21) Appl. No.: 16/233,053

(22) Filed: Dec. 26, 2018

(65) Prior Publication Data

US 2019/0147722 A1    May 16, 2019

Related U.S. Application Data

(63) Continuation of application No. 15/880,070, filed on Jan. 25, 2018, now Pat. No. 10,198,927, which is a (Continued)

(51) Int. Cl.
*H04W 4/02* (2018.01)
*G08B 21/04* (2006.01)
(Continued)

(52) U.S. Cl.
CPC .......... *G08B 21/043* (2013.01); *A61B 5/0024* (2013.01); *G08B 21/0261* (2013.01); *G08B 21/0272* (2013.01); *G08B 21/0446* (2013.01); *G08B 21/0461* (2013.01); *G08B 25/005* (2013.01); *H04W 4/023* (2013.01); *A61B 5/00* (2013.01); *A61B 5/0002* (2013.01); *A61B 5/0015* (2013.01); *A61B 5/103* (2013.01); *A61B 5/11* (2013.01); *G06Q 50/22* (2013.01); (Continued)

(58) Field of Classification Search
CPC ....... A61B 5/00; A61B 5/0002; A61B 5/0015; A61B 5/002; A61B 5/0022; A61B 5/0024; A61B 5/103; A61B 5/11; A61B 5/1112; A61B 5/1113; A61B 5/1114; A61B 5/1115; A61B 5/1116; A61B 5/1117; A61B 5/1118; G08B 21/00; G08B 21/02; G08B 21/043; G06Q 50/22; G06Q 50/24; G06Q 50/265
See application file for complete search history.

(56) References Cited

U.S. PATENT DOCUMENTS 8,549,028 B1 * 10/2013 Alon ..................... G06Q 50/265
                                                                707/769
2014/0114692 A1 * 4/2014 Pearce ................... G06Q 40/08
                                                                705/4

* cited by examiner

*Primary Examiner* — Benyam Haile

(57) ABSTRACT

One variation of a method for detecting and handling falls by residents of a facility includes: receiving a notification for a fall event from a first resident wearable device associated with a resident; determining a location of the resident within a facility at a time of the fall; in response to the notification, distributing a fall response prompt to a set of computing devices, each computing device associated with a care provider; and, in response to proximity of the first computing device to the first resident wearable device, authorizing edit permissions for an electronic incident report by a first care provider exclusive of a second care provider.

6 Claims, 5 Drawing Sheets

Related U.S. Application Data continuation of application No. 15/339,771, filed on Oct. 31, 2016, now Pat. No. 9,922,524.

(60) Provisional application No. 62/249,060, filed on Oct. 30, 2015.

(51) Int. Cl.
| | |
|---|---|
| *A61B 5/00* | (2006.01) |
| *G08B 21/02* | (2006.01) |
| *G08B 25/00* | (2006.01) |
| *A61B 5/11* | (2006.01) |
| *G06Q 50/24* | (2012.01) |
| *A61B 5/103* | (2006.01) |
| *G06Q 50/26* | (2012.01) |
| *G08B 21/00* | (2006.01) |
| *G06Q 50/22* | (2018.01) |
| *G16H 40/63* | (2018.01) |
| *G16H 10/60* | (2018.01) |

(52) U.S. Cl.
CPC ........... *G06Q 50/24* (2013.01); *G06Q 50/265* (2013.01); *G08B 21/00* (2013.01); *G08B 21/02* (2013.01); *G16H 10/60* (2018.01); *G16H 40/63* (2018.01)

METHODS FOR DETECTING AND HANDLING FALL AND PERIMETER BREACH EVENTS FOR RESIDENTS OF AN ASSISTED LIVING FACILITY

CROSS-REFERENCE TO RELATED APPLICATIONS

This Application is a continuation application of U.S. patent application Ser. No. 15/880,070, filed on 25 Jan. 2018, which is a continuation application of U.S. patent application Ser. No. 15/339,771, filed on 31 Oct. 2016, which claims the benefit of U.S. Provisional Application No. 62/249,060, filed on 30 Oct. 2015, all of which are incorporated in their entireties by this reference.

TECHNICAL FIELD

This invention relates generally to the field of senior and disabled care and more specifically to new and useful methods for detecting and handling fall and perimeter breach events for residents of an assisted living facility in the field of senior and disabled care.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Method

Figure 1:
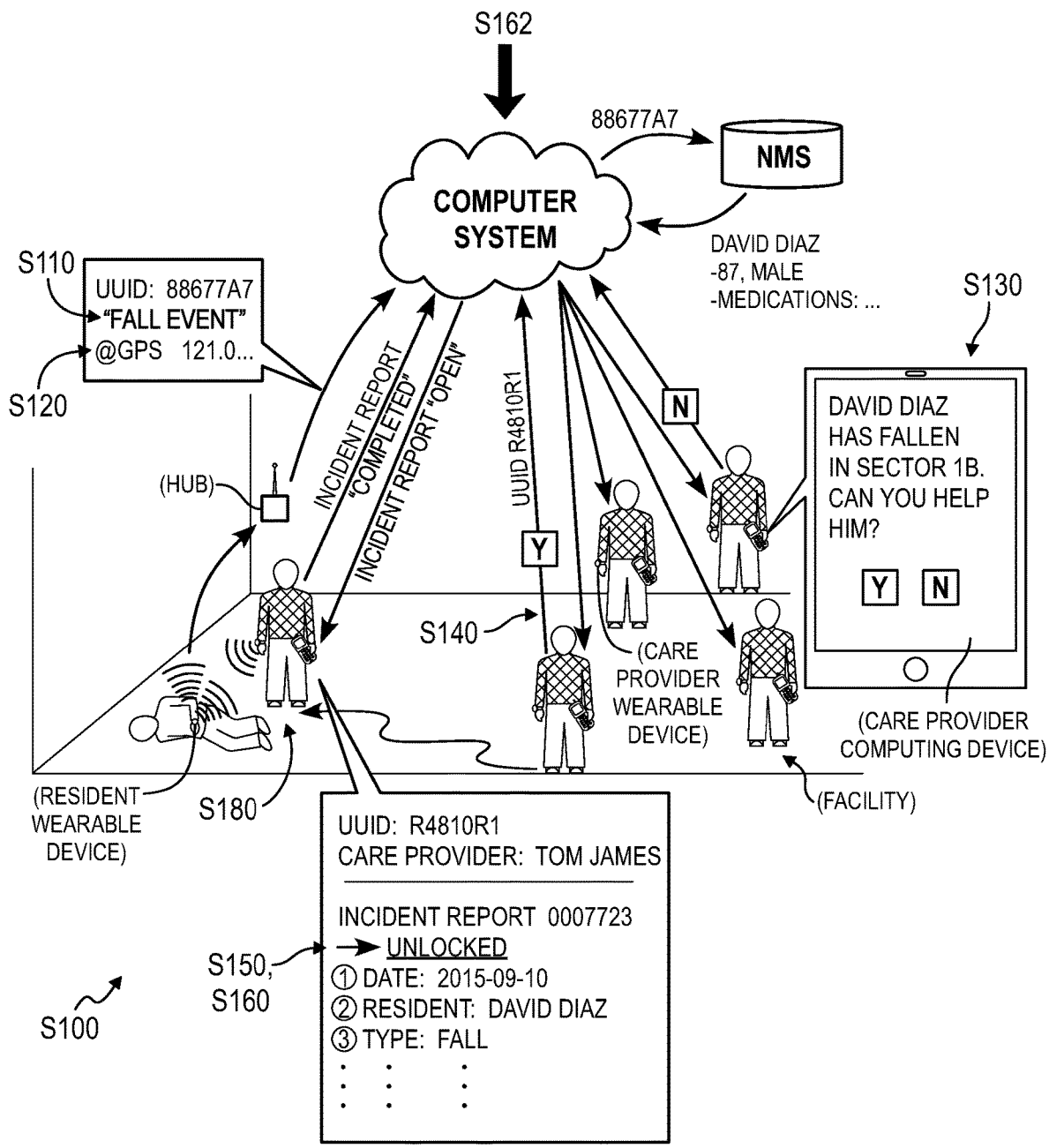
FIG. 1 is a flowchart representation of a method.

As shown in FIG. 1, a method S100 for detecting and handling falls by residents of an assisted living facility includes: receiving a notification for a fall event from a resident wearable device associated with a resident in Block S110; determining a location of the resident within a facility at a time of the fall event based on proximity of the resident wearable device to a wireless communication hub arranged at a known location within the assisted living facility in Block S112; in response to the notification, distributing a fall response prompt to a set of computing devices within the facility, each computing device in the set of computing devices associated with a care provider, the fall response prompt indicating the location in Block S130; in response to receipt of a fall response confirmation from a first computing device within the set of computing devices, deescalating the fall response prompt at a second computing device within the set of computing devices in Block S140; in response to proximity of the first computing device to the resident wearable device, authorizing edit permissions for an electronic incident report by a first care provider associated with the first computing device exclusive of a second care provider associated with the second computing device in Block S150.

Figure 2:
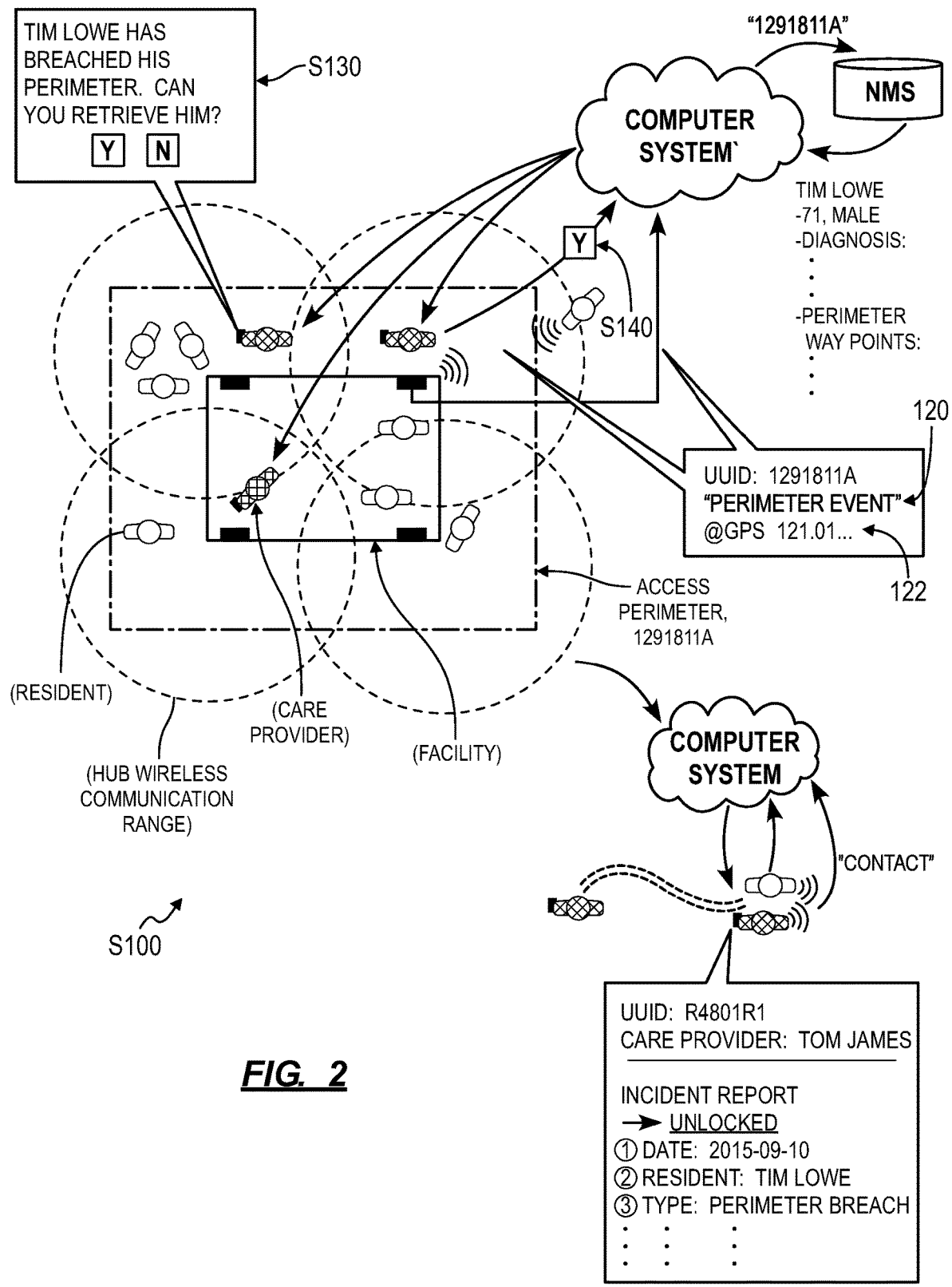
FIG. 2 is a flowchart representation of one variation of the method.

As shown in FIG. 2, one variation of the method S100 includes: assigning a first access perimeter within the facility to a first occupant; at a first time, determining a location of a occupant wearable device associated with the first occupant based on wireless communications between the occupant wearable device and a set of wireless communication hubs within the facility; in response to the location of the occupant wearable device falling outside of the access perimeter, distributing a perimeter event prompt indicating the location of the first occupant to a set of computing devices, each computing device in the set of computing devices associated with a care provider affiliated with the facility; in response to receipt of a perimeter event confirmation from a first computing device within the set of computing devices, deescalating the perimeter event prompt at a second computing device within the set of computing devices; in response to proximity of the first computing device to the occupant wearable device, authorizing edit permissions for an electronic incident report by a first care provider associated with the first computing device exclusive of a second care provider associated with the second computing device.

2. Applications

Generally, the method S100 can be implemented within or in cooperation with an assisted living facility to provide real-time prompts to care providers in support of care for residents of the assisted living facility. In particular, a computer system implementing Blocks of the method S100 can interface with wearable devices assigned to residents of the facility to detect instances in which residents of the assisted living facility fall ("fall events") and/or move beyond assigned perimeters within or around the facility ("perimeter events"). The computer system can respond to these events by transmitting prompts and fall or perimeter event details to care providers within the facility substantially in real-time. The computer system can also track care provider responses to these prompts and provide guidance to care providers when responding to and reporting results of such fall and perimeter breach events.

Blocks of the method S100 can therefore be executed by a computer system, such as on a local computer system within an assisted living facility (e.g., a local server), by a remote server in the cloud, or by a distributed computer network (hereinafter "computer system"). In particular, the computer system can interface with multiple devices within and around the assisted living facility (the facility") to handle and respond to fall events and/or proximity events for residents of the facility.

The method S100 is described herein as implemented within or in conjunction with an assisted living facility. However, the method S100 can be similarly implemented within a general hospital, a psychiatric hospital, a preschool, a summer camp, or any other health institution, clinic, or community. Similarly, the method S100 is described below as implemented by a facility to serve a resident of the facility, though the method S100 can additionally or alternatively be implemented to serve a patient at a general hospital, a student at a school, or a child at a day care or summer camp, etc. The method S100 can be similarly implemented by a facility to guide a care provider—such as a nurse, a teacher, or a camp counselor—to serve such residents, patients, or students, etc.

3. Devices

As shown in FIGS. 1 and 2, Blocks of the method S100 can be executed by a local or remote computer system that interfaces with a set of wearable devices assigned to a group of residents and to a group of care providers, one or more wireless communication hubs within or around an assisted living facility, and/or a set of computing devices assigned to the group of care providers.

Figure 3:
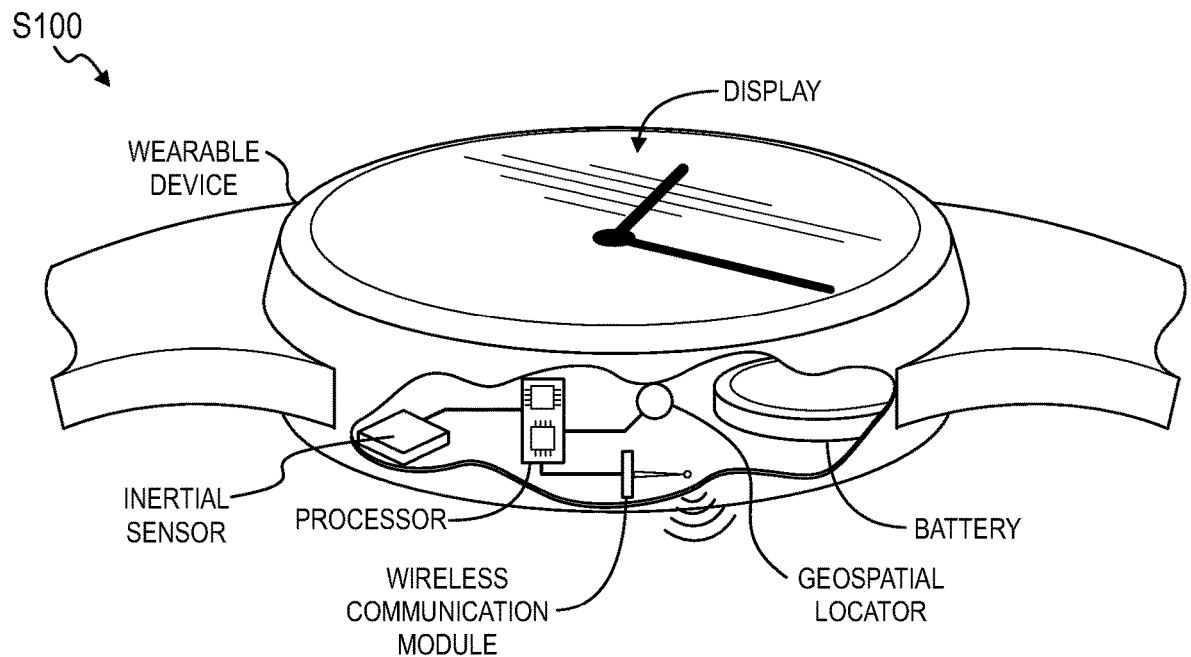
FIG. 3 is a schematic representation of a resident wearable device.

In one implementation, an administrator of the assisted living facility (hereinafter "facility") can access an administrator interface to assign a resident of the facility one or more (i.e., a set of) wearable devices. In one example, the administrator assigns a resident two wearable devices, including: a first wearable device to be worn by the resident during the day and recharged and night; and a second wearable device to be worn by the resident at night and recharged during the day. Each resident wearable device can be loaded with a unique ID (e.g., a UUID), and the unique ID can be associated with a particular resident of the facility, such as in a name mapping server (or "NMS"), as shown in FIGS. 1 and 2. In this implementation, the resident wearable device can include: a set of inertial sensors; a processor configured to detect fall events based on outputs of the inertial sensor(s); a geospatial location sensor (e.g., a GPS sensor); a wireless communication module that broadcasts fall event data and location data; and/or a rechargeable battery that powers the foregoing elements, as shown in FIG. 3.

Figure 4:
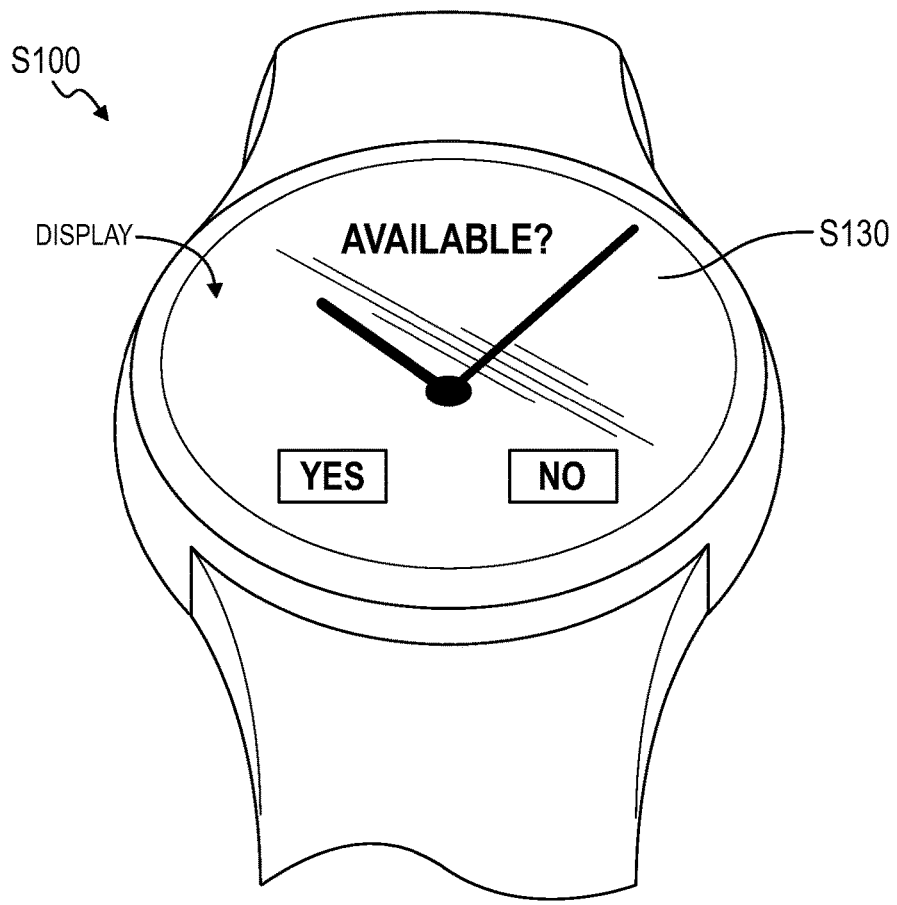
FIG. 4 is a schematic representation of a care provider wearable device.

In the foregoing implementation, the administrator of the assisted living facility can assign or otherwise provide a care provider—employed by the facility—with one or more care provider wearable devices and/or computing devices. A care provider wearable device can be substantially similar to the resident wearable device, as described above. The wearable device can additionally or alternatively include: a short-range wireless communication module (e.g., a low power 2.4 GHz wireless communication device); an inertial sensor (e.g., an accelerometer); an input field (e.g., a touchscreen); a processor; and/or a rechargeable battery. The processor can implement "proximity card" methods to confirm that the care provider has made contact with the resident based on outputs of the inertial sensor, such as when a care provider taps his wearable device to a wearable device worn by a resident while or after responding to a fall or perimeter event, as described below. Each care provider wearable device can also be assigned and can store in local memory a unique ID (e.g., a UUID), and each care provider wearable device ID can be associated with a particular care provider at the facility, such as in a NMS. A care provider wearable device ID can also be associated with a set of information corresponding to a care provider assigned to the care provider wearable device, such as the care provider's name, care provider facility ID, gender, age, specialty (e.g., manual assistance, nurse, physical therapist, pharmacist, doctor, administrator), etc. Furthermore, a care provider wearable device can include a digital user interface (e.g., a display); the care provider wearable device can render a prompt to respond to a fall event or to a perimeter breach event and can receive a response to this prompt from a corresponding care provider through the display, as shown in FIG. 4.

Figure 5:
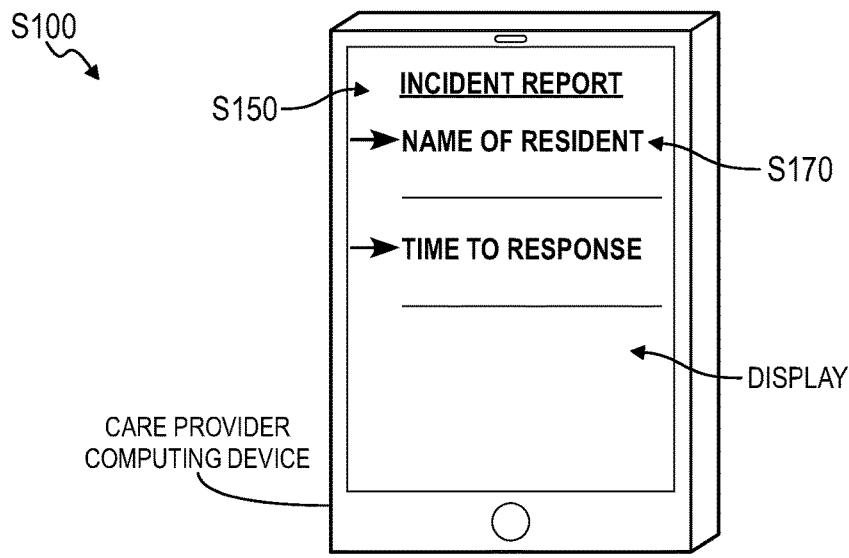
FIG. 5 is a graphic representation of one variation of the method.

As shown in FIG. 5, a computing device (e.g., a tablet or a smartphone) assigned to a care provider can execute a native care provider application, as described below. For example, the native care provider application can: receive an event prompt from a local or remote server; alert a care provider of the event prompt through a user interface (e.g., on an integrated display); receive a response to the event prompt (e.g., "Yes, I will respond" or "No, I cannot respond right now") from the care provider through the user interface; upload the event prompt responses to the remote server; serve an incident report to the care provider through the interface; collect data entered into the incident report manually by the care provider; and communicate these data back to the server.

Additionally or alternatively, an instance of the native care provider application can be installed on a private computing device owned by a care provider, such as the care provider's personal smartphone or tablet.

Similarly, a computing device (e.g., a tablet or a smartphone) associated with a resident can execute a native resident application, as described below, which can: receive a fall or perimeter response prompt from a local or remote server; present this response prompt to the resident through a user interface (e.g., on its integrated display); receive a response to the event prompt fro the resident, such as "Yes, I have fallen and need assistance" or "No, I have not fallen and do not need assistance"; and upload the resident's responses to the local or remote server.

4. Fall Detection

Block S110 of the method S100 recites receiving notification of a fall event from a resident wearable device associated with a resident. Generally, in Block S110, the computer system can receive a notification broadcast wirelessly from the resident's wearable device and indicate that the resident experienced a fall event.

In one implementation, the resident wearable device samples an accelerometer, a gyroscope, a tilt sensor, an impact sensor, a barometric pressure sensor, and/or any other suitable sensor or set of sensors over time while the resident wearable device is being worn and can manipulate these data to determine if the user has fallen—that is, to determine a fall event. In response to detection of a fall event, the wearable device can broadcast a flag, alarm, or notification indicating the fall event. A local wireless communication hub can receive this signal from the resident's wearable device and route this flag, alarm, or notification to the computer system. Alternatively, if the resident wearable device is out of range of a wireless communication hub, other devices (e.g., resident and/or care provider wearable devices, resident-assigned computing devices, etc.) can cooperate to form a distributed network within the facility and can collect and can route the flag, alarm, or notification to a nearby wireless communication hub for distribution to the computer system.

In one implementation, a resident wearable device can maintain and execute a fall detection model including an artificial neural network (e.g., a recurrent artificial neural network with Gated Recurrent Units (GRU) or Long Short Term Memory (LSTM) defining a set of connections, neurons, and layers through which a sensor packet from a wearable device can be passed to output a determination of presence of absence of a fall event at the wearable device. (A data packet described herein can include one or more sensor output values from a single sampling period or a sequence or pattern of sensor output values collected at the wearable device over multiple sampling periods.) The wearable device can thus pass sensor data into the locally-stored fall detection model to detect falls by a resident wearing the wearable device.

During operation, the resident wearable device can regularly execute the locally-stored fall detection model to transform sensor data sampled from a set of sensors integrated into the wearable device—such as motion data from an accelerometer and pressure data from a barometric pressure sensor—into a first level of confidence (hereinafter a "confidence score") that a fall event occurred at a resident wearing the wearable device. For example, the locally-stored fall detection model can output a confidence score for occurrence of a fall event at each sampling period, thereby creating a series of fall event confidence scores over time. The wearable device can then confirm a fall event locally at the wearable device in response to a minimum number of consecutive fall event confidence scores output by the locally-stored fall detection model exceeding a confidence threshold. The fall detection model can also detect a fall event in response to a more than a threshold proportion (e.g., 90%) fall event confidence scores in a sequence of confidence scores exceeding a fall event confidence threshold. In response to detecting a fall event, the wearable device can thus upload a fall event notification to the remote computer system.

In this implementation, the resident wearable device can store and execute a compressed (i.e., reduced size) version of the fall detection model. When the wearable device detects a fall event based on an output of the compressed fall detection model, the wearable device can upload recent sensor data to the remote computer system in addition to a fall event notification. The remote computer system can execute a complete (e.g., non-reduced) version of the fall detection model and can pass these sensor data into the complete fall detection model to confirm or invalidate the fall event detected by the wearable device. For example, in response to an output of the compressed fall event model indicating occurrence of a fall event, the resident wearable device can transmit sensor data collected locally to a nearby wireless communication hub, which can in turn upload these data to the computer system. The remote computer system can then execute the complete version of the fall detection model to recalculate a fall event confidence score from these sensor data. The wearable device and the remote computer system—executing the compressed and complete fall detection models, respectively—can cooperate to confirm fall events at the wearable device with a high degree of precision despite limited and intermittent communication between the wearable device and the remote computer system. In this example, the computer system can then generate and distribute a fall response prompt in Block S130, as described below, after confirming a fall event, such as in response to an output of the enlarged form of the compressed fall detection model (e.g., the complete version of the fall detection model) exceeding the threshold confidence score over a threshold period of time.

In the foregoing implementation, the resident's wearable device can also estimate a magnitude of the fall event based on signals output from internal sensors before, during, and/or after the fall event and then transmit these data to the computer system. The computer system can then set a minimum number of care providers needed to respond to the fall event based on (e.g., proportional to) the magnitude of the fall. The computer system can also select one or more types of care providers to respond to the fall event, such as any care provider for a fall of low impact magnitude, a nurse for a fall of moderate impact magnitude, and an internal medicine physician or an orthopedic surgeon for a fall of high impact magnitude. Furthermore, the computer system can incorporate a quantitative and/or qualitative indicator of the magnitude of the fall into the fall response prompt that is distributed to care providers within the facility in Block S130. For example, the computer system can categorize the magnitude of a fall as low, moderate, or high.

5. Location

Block S112 of the method S100 recites determining a location of the resident within the facility at a time of the fall event based on proximity of the resident wearable device to a wireless communication hub arranged at a known location within the assisted living facility. Generally, in Block S112, the computer system cooperates with the resident's wearable device, one or more local wireless communication hubs, and/or any other device within proximity of the resident's wearable device to determine the location of the resident at the time of the fall event (and at times succeeding the fall event).

In one implementation, in response to detecting a fall event, the resident's wearable device can regularly broadcast a test signal to one or more local wireless communication hubs of known location(s) within the facility. The resident wearable device can then receive return signals and wireless IDs (e.g., UUIDs) from the wireless communication hub(s), calculate a flight time for the test signal, and transmit these wireless IDs and corresponding flight times of the test signals (via a local wireless hub) to the computer system, which can then reconstruct the location of the resident's wearable device—and therefore the resident—from these data. For example, if a single wireless communication hub is within wireless range of the resident's wearable device, the computer system can determine that the resident is within a circular area centered at the known location of the wireless communication hub by: referencing the UUID received from the wireless communication hub to a map of the facility; and calculating the radius of the circular area based on the flight time of a test signal broadcast by the wearable device and then received from the wireless communication hub. In this example, the computer system can later generate a fall response prompt that indicates that the resident is located within the circular area, as described below.

In the foregoing implementation, the resident wearable device can also: collect UUIDs and test signal flight times from two or more local wireless communication hubs; and transmit these UUIDs and test signal flight times together with a fall event notification to computer system via a local wireless communication hub. The computer system can then implement similar techniques to determine the location of the resident within the facially, such as by triangulating the position of the resident's wearable device within the facility relative to the three (or more) wireless communication hubs. The computer system can also triangulate the resident's wearable device based on proximity to other devices within the facility, such as based on flight times of test signals broadcast by the resident's wearable device and returned from other resident wearable devices, care provider wearable devices, and/or computing devices within the facility. The computer system can then incorporate location areas or location points of a fall event within the facility into the fall response prompt transmitted to care providers within the facility in Block S130.

In another implementation, the computer system implements similar methods and techniques to determine the location (e.g., a point, an area) of the resident's wearable device based on time of flight data received from one or more wireless communication hubs and/or other wireless-enabled devices in communication with the resident's wearable device (e.g., a mobile computing device associated with the resident and communicatively coupled to the resident wearable device) at the time of a fall event. Alternatively, the computer system can determine the location of the resident's wearable device based on signal strength data received from one or more wireless communication hub and/or other wireless-enabled devices in communication with the resident's wearable device at the time of the fall. For example, the computer system can retrieve a first wireless signal strength for wireless communications between the resident wearable device and a first wireless communication hub; retrieve a second wireless signal strength of wireless communications between the resident wearable device and a second wireless communication hub; transform the first and second wireless signal strengths into a position of the resident wearable device relative to the first and second wireless communication hubs; and transform the position of the resident wearable device into a region of the facility likely occupied by the resident.

In the foregoing implementations, the resident wearable device can maintain constant communication with a wireless communication hub while within wireless range of the wireless communication hub and can broadcast sensor data and fall event notifications to this wireless communication hub at regular intervals, such as at a rate of 20 Hz. Alternatively, the resident wearable device can wirelessly connect to one or more local wireless communication hubs intermittently, such as: once per second; once per second while the resident is determined—by the wearable device—to be moving; and/or once per minute while the resident is determined to be stationary. In this example, the resident wearable device can store sensor data in a local buffer and upload data from the buffer to a local wireless communication hub for remote processing each time the wearable device and hub connect and before clearing the buffer.

Furthermore, in response to detecting a fall event, the resident's wearable device can collect location-related data and transmit these data to the computer system, such as via the wireless communication hub as described above, for incorporation into a fall response prompt in Block S130. For example, for the resident wearable device that includes a geographic location sensor, the resident wearable device can sample the geographic location sensor and transmit a result from the geographic location sensor to the computer system. The computer system can then incorporate this geographic location into fall response prompts transmitted to care providers in Block S130, and instances of a native care provider application can render this resident's location on a virtual map of the facility.

However, the resident's wearable device, the wireless communication hub(s), and/or the computer system can cooperate in any other way to determine the location of the resident's wearable device at or near the time of the fall event.

6. Fall Response Prompts

Block S130 of the method S100 recites, based on the notification, distributing a fall response prompt to a set of computing devices within the facility, each computing device in the set of computing devices associated with a care provider, the fall response indicating the location. Generally, in Block S130, the computer system generates a fall response prompt and transmits (e.g., "distributes," "disperses," "disburses") instances of this prompt to care providers within (e.g., occupying, employed by) the facility in response to receipt of a fall event notification from a resident wearable device.

In one implementation, in response to receipt of a fall event notification from a resident wearable device (e.g., through a local wireless communication hub), the computer system can pass a UUID (or other identifier or address) received with the fall event notification into a lookup table to retrieve the resident's name. The computer system can also retrieve the resident's age, gender, preferred nickname, and/or health status (e.g., diagnosed medical conditions, existing prescriptions, mental health condition) as well as a digital photograph of the resident, such as from a remote database. The computer system can then aggregate any of these data, a time of receipt of the fall event notification, a magnitude of the fall, and a location of the resident (e.g., a point or region of the facility likely occupied by the resident) currently and/or at a time of the fall into a virtual fall response prompt including a request that a care provider assist the resident in getting up and respond to any trauma that the resident may have experienced during the fall event. Upon receipt of a fall response prompt at a computing device or at a care provider wearable device, a care provider can thus readily access the location of the resident, the resident's name, an image of the resident, and/or a fall magnitude—and therefore a possible magnitude of the resident's trauma—for the fall event from the fall response prompt.

6.1 Fall Response Recipients

Once the fall response prompt is thus generated, the computer system can distribute the fall response prompt to all active care providers within the facility. In one example, the computer system retrieves a facility schedule, identifies care providers (e.g., by name, employee number, etc.) currently on duty based on current time and the facility schedule, and passes care provider identities through a reverse-lookup table to retrieve an address (e.g., a UUID, a username, a phone number, or an email address) for a computing device and/or a care provider wearable device for each employee currently on duty. The computer system can then transmit an instance of the fall response prompt to each computing device and/or to each care provider wearable device thus identified.

The computer system can also filter care providers currently on duty based on the resident's immediate needs. In one example, the computer system filters the list of care providers currently on duty based on proximity to the resident at the time of the fall event. In this example, the computer system can request location data (e.g., GPS location data, the location of a nearest hub) from care provider wearable devices and/or care provider-assigned computing devices associated with care providers currently on duty and then select a number (e.g., ten) care providers nearest the resident or select all care providers within a threshold distance (e.g., 100 meters) of the resident and then transmit the fall response prompt to only these select care providers. The computer system can then distribute a fall response prompt to a set of computing devices assigned to care providers likely to be in the vicinity of the fallen resident. Furthermore, in this example, the computer system can adjust number or proximity settings for selecting recipients of the fall response prompt based on an amount of time since the fall event was detected (e.g., by expanding the proximity limit as more time expires since the fall event), based on a number of fall event prompts transmitted to care providers in the facility before a positive fall response confirmation is received, or based on any other relevant factor.

In one example, the computer system can: implement methods and techniques described above to determine positions of computing devices in a group of computing devices assigned to care providers occupying the facility based on wireless communications between the group of computing devices and wireless communication hubs arranged within the facility; select a set of computing devices—from the group of computing devices—occupying a position within a threshold distance of the location of the occupant at the time of the fall event; and transmit the fall response prompt to each computing device in the set.

In another example, the computer system selects recipients of the fall response prompt based on response histories of care providers currently on duty. In this example, the computer system can process response histories of care providers employed by the facility to identify care providers who have provided the most rapid and/or best care to fallen residents and properly completed incident reports, and the computer system can transmit instances of the fall response prompt to these select care providers.

In yet another example, the computer system selects recipients of the fall response based on known relationships between care providers and residents. In this example, the computer system can: identify a care provider currently on duty and who has been assigned as the primary care provider for the fallen resident; and then transmit the fall response prompt to the select care provider. Similarly, the computer system can identify a particular care provider not currently on duty but who has been assigned as the primary care provider for the fallen resident and transmit fall data to the particular care provider in addition to transmitting the fall response prompt to other care providers currently on duty within the facility.

In another example, the computer system selects recipients of the fall response prompt based on care provider activity levels around the time of the fall event. In this example, the computer system can request motion type and/or activity intensity (e.g., sitting, standing, walking, or running activity types; low, moderate, high activity intensities) data from each all or select care providers currently on duty within the facility and selects only a subset of care providers who are sitting, standard, or walking at a low or moderate intensity as recipients of the fall response prompt; the system can thus withhold the fall response prompt from care providers who are running, walking at high intensities, or otherwise busy.

In still another example, the computer system selects recipients of the fall response prompt based on skills of the care providers and needs of the resident. In this example, the computer system can retrieve the size (e.g., weight, height, etc.) and a list of physical disabilities of the resident from a resident database; the computer system can also retrieve a recorded capacity to lift (e.g., low, average, high lifting ability) of each care provider currently on duty. The computer system can then select only care providers who weigh at least a particular multiplicative factor of the resident's weight, such as care providers who weight at least 180 pounds for a resident who weighs 150 pounds in order to satisfy a multiplicative factor of 1.2. Based on the resident's weight, the computer system can also set a minimum number of care providers to respond to the fall prompt response, such as one care provider for a resident who weighs less than 150 pounds, two care providers for a resident who weighs between 150 and 250 pounds, three care providers for a resident who weighs between 250 and 350 pounds.

However, the computer system can filter and select recipients of the fall response prompt according to any other single or combination of schema.

For care providers thus selected to receive a fall response prompt for the fall event, the computer system can also customize the fall response prompt for a care provider. For example, for a first care provider currently on duty within the facility and selected to respond to a fall event, the computer system can: request a location (e.g., a GPS location, a nearest wireless communication hub within the facility) from a computing device or from a care provider wearable device associated with the first care provider; generate a fastest walking path between the location of the first care provider and the resident at the time of the fall event; and insert a map of the facility and a visual representation of this path into a custom fall response prompt for the first care provider. When the custom fall response prompt is then delivered to the first care provider, the care provider can open the fall response prompt and quickly access a map or floor plan route to the resident.

Alternatively, a native care provider application executing on the first care provider's computing device can implement similar methods and techniques to generate a recommended route from the first care provider's current location to the resident, such as in response to receipt of a fall response prompt or in response to receipt of a confirmation that the first care provider will respond to the fall event. The native care provider application can also show the locations of other care providers within the facility and their relative distances from the resident. For example, a first care provider reviewing the fall response prompt can thus relatively quickly access identifying information of other care providers that first care provider may gather to assist the resident as he heads toward the resident's location.

6.2 Fall Response Prompt Confirmation

Block S140 of the method S100 recites, in response to receipt of a fall response confirmation from a first computing device within the set of computing devices, cancelling the fall response prompt at a second computing device within the set of computing devices. Generally, in Block S140, the computer system functions to: receive confirmation from a particular care provider that he (or she) will assist the resident; to dispatch the particular care provider to the resident; and to withdraw fall response prompts from other recipients of the fall response prompt.

In one implementation, a native care provider application executing on a computing device assigned to and carried by a care provider renders—on a display of the computing device—a virtual fall response prompt with a first virtual input region exhibiting a positive response (e.g., "Yes, I will respond") and a second virtual region exhibiting a negative response (e.g., "No, I cannot respond right now"). In this implementation, in response to selection of the first virtual region, the native care provider application can return a positive fall response confirmation to the computer system. Alternatively, the native care provider application can receive an instance of the positive or negative response to the fall response prompt through an associated care provider wearable device wirelessly, and the native care provider application can then transmit this response (or only positive responses) to the computer system. Yet alternatively, the computer system can collect positive and/or negative responses to the fall response prompt directly from care provider wearable devices, such as routed through local wireless communication hubs rather than through associated computing devices. Upon receipt of positive confirmation for the fall response prompt from a particular (e.g., the first) care provider, the computer system can then immediately transmit a cancellation notice to each other recipient of the fall response prompt (e.g., the second care provider and other care providers in the facility).

Alternatively, upon receipt of positive confirmation for the fall response prompt from a particular care provider, the computer system can immediately transmit a notification indicating—to each other recipient of the fall response prompt—that the particular care provider will respond to the prompt and/or indicating that the fall response prompt has been placed at a lower priority level. Later, the computer system can also transmit a cancellation notice to each other recipient of the fall response prompt upon completion of the fall response by the respondent care provider, such as indicated by submission of an incident report for the fall event. The computer system can additionally or alternatively, upon receipt of positive confirmation for the fall response prompt from a particular care provider, deescalate the fall response prompt by silencing the fall response prompt at the computing devices of each other recipient of the fall response prompt.

Once a particular care provider submits confirmation that he will respond to the fall response prompt, the computer system can also pull location data from the computing device and/or from the care provider wearable device assigned to the particular care provider. The computer system can then track the care provider's progress toward the recipient and cancel the fall response prompt at other devices within the facility if the particular care provider is moving toward the resident, reaches the resident, or reaches a threshold distance from the resident.

Furthermore, for fall events necessitating two or more responders, the computer system can set the fall response prompt to persist until at least the requisite number of care providers submit positive confirmation of response to the fall response prompt. The computer system can also issue directives to a care provider electing the fall response prompt based on the requisite number of care providers for the fall event and a number of positive responses received from recipients of the fall response prompt. For example, if the computer system determines that two care providers are required to respond to a fall event due to the weight and size of the resident, the computer system can issue a secondary prompt to a first care provider (e.g., transmit a notification to a computing device assigned to the first care provider) to not attempt to lift the resident until confirmation is received from a second care provider in the facility; the computer system can then retract the secondary prompt once a second care provider elects to help the resident and/or once a computing device or care provider wearable device assigned to a second care provider arrives at the resident's location. (An instance of the native care provider application executing on a care provider's computing device can additionally or alternatively implement these methods and techniques locally.)

During both fall events and perimeter breach events (as described below), the resident's wearable device can broadcast the resident's heart rate, heart rate variability, skin temperature, and/or other physiological signals, and the computer system can transmit these physiological data to a care provider within the facility while a fall response prompt or while a perimeter response prompt is active. For example, after receiving positive confirmation from a care provider in response to a fall event prompt, the computer system can regularly transmit the resident's heart rate to the care provider (e.g., through the native care provider application executed on a mobile computing device associated with the care provider) until the computer system receives verification (as described below) that the care provider has arrived at the resident's location.

6.3 Fall Response Cancellation

In one implementation, the computer system can receive a cancellation request for the fall response prompt from the resident for which the fall response prompt was generated. For example, the resident wearable device may falsely identify that the resident has fallen (i.e., a false positive fall event), or the resident may actually have fallen (i.e., a true positive fall event) but is not hurt and does not need help. In such cases, the resident may request cancellation the fall response prompt by pressing a button on her wearable device. Upon receipt of a fall response prompt cancellation request from the resident's wearable device, the computer system can transmit a cancellation notice to recipients of the outstanding fall response prompt.

In one implementation, the computer system can determine a magnitude of the fall event and can handle the fall response cancellation request accordingly. For example, the computer system (or the resident's wearable device) can transform accelerometer and/or gyroscope data collected at the wearable device during the fall event into a magnitude of the fall event, such as proportional to a peak acceleration (or deceleration) during the fall event. In this example, if the magnitude of the fall is determined to be low (e.g., below a low threshold magnitude), the computer system can approve the fall response cancellation request and transmit a cancellation notice to recipients of the outstanding fall response prompt. If the magnitude of the fall is determined to be moderate (e.g., above a low threshold magnitude and below a high threshold magnitude), the computer system can approve the fall response prompt cancellation request and transmit a cancellation notice to recipients of the fall response prompt while also flagging the resident for observation at a later time, such as by issuing a prompt to a nurse or other care provider at the facility to check in with the resident during the resident's next meal or when the resident is bedding down at the end of the same day or by automatically scheduling an appointment between the resident and a nurse, doctor, or other care provider at the facility within 48 hours. However, if the magnitude of the fall is determined to be high, the computer system can deny the fall response prompt cancellation request and persist the fall response prompt. In another example, in response to receipt of a fall response prompt cancellation request from the resident and determination that the fall was of a low magnitude, the computer system can persist the fall response prompt for a primary care provider assigned to the resident, reduce the priority of this fall response prompt, and transmit a cancellation notice to each other recipient of the fall response prompt. In this example, the primary care provider can thus check in with or observe the resident for trauma at a later, more convenient time.

In another implementation, in response to a fall response prompt cancellation request, a native resident application executing on a computing device associated with (e.g., carried by) the resident renders—on a display of the computing device—a virtual questionnaire (i.e., prompt) related to the fall event. For example, the virtual questionnaire can prompt the resident to confirm or deny the fall event, to indicate if the resident is or is not injured, and/or to indicate whether the resident is in need of help. In another example, in response to a fall response prompt cancellation request, the computer system can identify a second resident determined to be in the vicinity of the fall event (e.g., a witness) and transmit a virtual questionnaire to a computing device associated with the second resident. The native resident application can then render—on a display of the computing device—the virtual questionnaire, which can prompt the second resident to confirm or deny the fall event, to indicate if the (first) resident is or is not injured, and/or to indicate whether the (first) resident is in need of help. The computer system can then silence, deescalate, or persist the fall event prompt based on feedback from the second resident.

The computer system can thus cooperate with computing devices and wearable devices associated with residents of the facility to collect fall-related feedback from residents, such as through virtual questionnaires; the computer system can then label sensor data received from a resident during a fall event with this resident-entered feedback and then retrain the fall detection model (e.g., the compressed fall detection model implemented by resident wearable devices and the complete fall detection model implanted by the computer system) based on these labeled sensor data to reduce false positive fall events, as described below.

6.4 Fall Response Prompt Escalation

Figure 6:
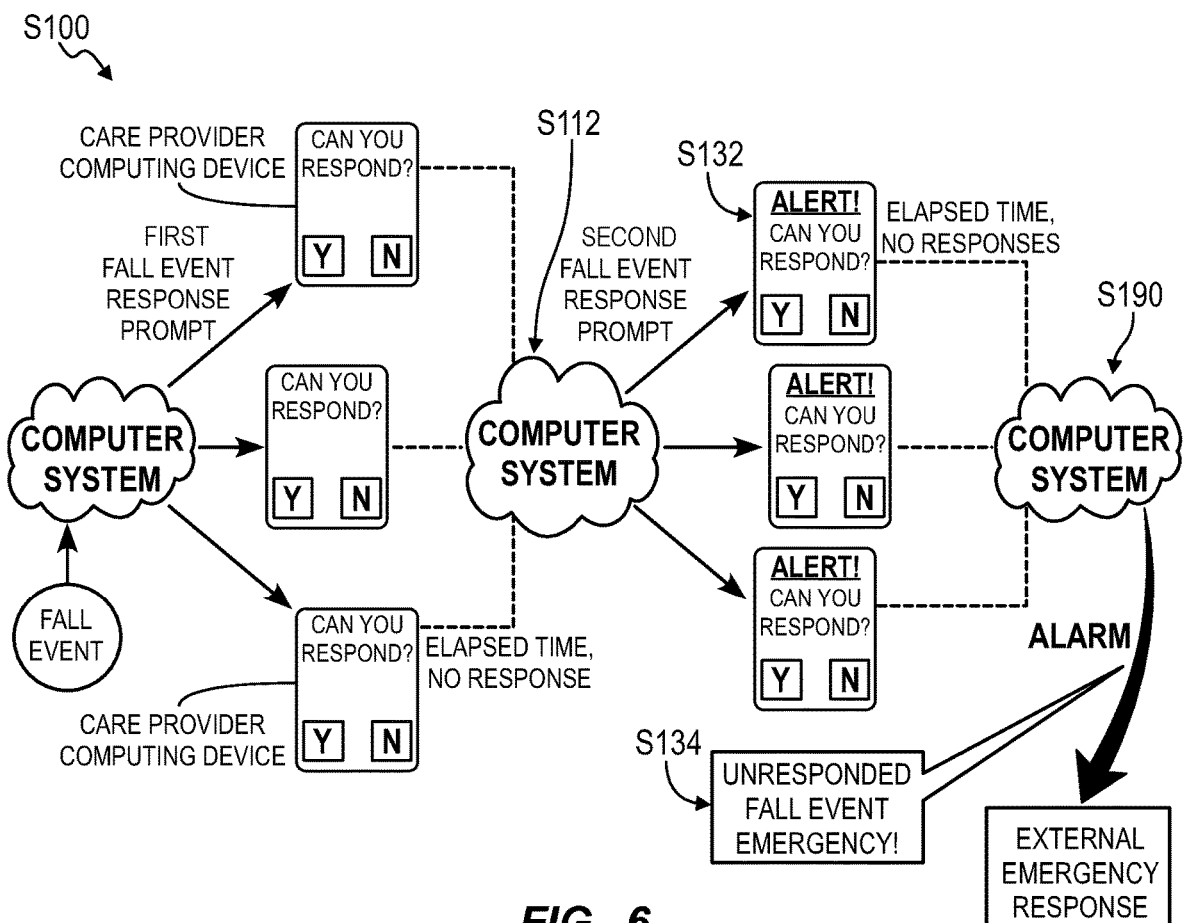
FIG. 6 is a flowchart representation of one variation of the method.

As shown in FIG. 6, one variation of the method S100 includes Block S132, which recites, in response to absence of a fall response confirmation from a computing device in the set of computing devices within a threshold period of time from distribution of the fall response prompt to the set of computing devices, distributing a second fall response prompt to the set of computing devices. The computer system can therefore issue additional prompts—of escalated priority—to care providers in the facility if no confirmation for response to a fall event (or to a proximity event) is received.

In one implementation, in response to absence of a fall response confirmation, the computer system can escalate the fall response prompt by distributing an additional fall response to additional care providers. For example, in response to absence of a fall response confirmation within a threshold period time following the distribution of the fall response prompt, the computer system can distribute a second fall response prompt to a second set of computing devices including a computing device associated with a supervisor of the facility. In particular, the computer system can grow a number of recipients of a fall event prompt as time progresses without fall response confirmation from a care provider. In another example, the computer system can: first distribute the fall response prompt to care providers on the same floor as and within 200 feet of the fallen resident; then distribute the fall response prompt to all care providers on the same floor as the fallen resident if no fall response confirmation is received within two minutes; then distribute the fall response prompt to all care providers within the facility if no fall response confirmation is received within the next two minutes; distribute the fall response prompt to all care providers within the facility and their managers if no fall response confirmation is received within the following two minutes; and then distribute the fall response prompt to all care providers within the facility, their managers, and administrators of the facility if no fall response confirmation is received within the subsequent two minutes.

In this variation, the method S100 can include Block S134, which recites, in response to the absence of a fall response confirmation from a computing device in the set of computing devices within a threshold period of time from distribution of the second fall response prompt to the set of computing devices, transmitting an alarm to an external emergency responder. Generally, in Block 134, if care providers within the facility consistently fail to reach the resident (i.e., if no proximity confirmation is received) despite distribution of multiple fall response prompts (or proximity event prompts) to the care provider's computing devices and wearable devices and despite receipt of one or more fall response confirmations from the care providers, the computer system can implement methods and techniques similar to those described above to notify an external (i.e., third-party) emergency responder of a resident's fall event (or proximity event).

The computer system can therefore actively monitor lack of responses and/or unfilled responses to fall responses prompts and issue additional fall response prompts and/or prompt involvement by a third-party responder to assist the resident after a fall.

The computer system can also escalate the fall response prompt, such as described above, in response to an input from the fallen resident at the resident's wearable device. For example, the resident wearable device can include a "fall" or "help" button, and the computer system can escalate the fall response prompt one level each time the resident depresses the "fall" or "help" button or escalate the fall response prompt one level once per two-minute period in which the resident depresses the "fall" or "help" button. However, the computer system can escalate (or deescalate) the fall response prompt in any other way and in response to any other action or event.

7. Perimeter Breach

One variation of the method S100 includes Block S120, which recites assigning an access perimeter within a facility to a resident. Generally, in Block S120, the computer system assigns an access perimeter within or around the facility to all or a subset residents of the facility, such as an absolute geospatial access perimeter or an access perimeter defined by wireless communication hubs installed throughout the facility. For example, the computer system can implement geofencing techniques to assign an access perimeter to a resident within the facility.

7.1 Access Perimeters

Figure 7:
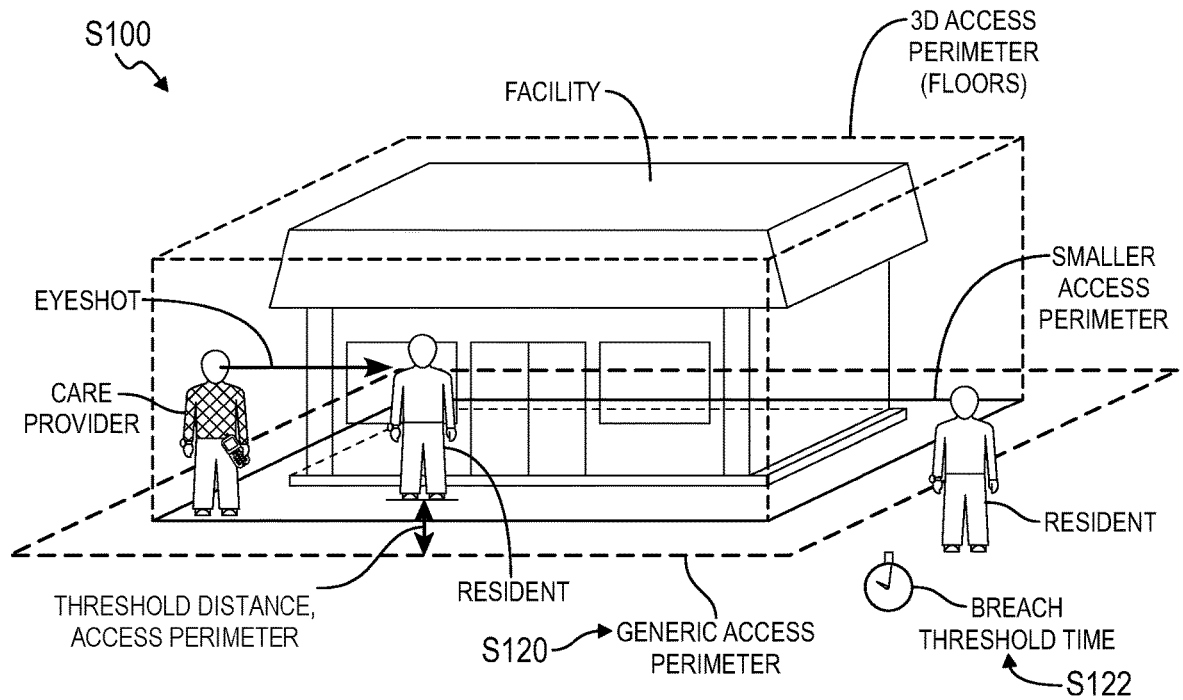
FIG. 7 is a flowchart representation of one variation of the method.

In one implementation, an administrator of the facility can access an administrator interface hosted by the computer system, such as through a web browser, to select waypoints around the facility from a virtual geospatial map; the computer system can then transform these waypoints into a polygonal access perimeter within or around the facility, as shown in FIG. 7. Based on a selection submitted by the administrator through the administrator interface, the computer system can set a trigger to issue a perimeter breach alarm for all or a subset residents of the facility.

The computer system can similarly cooperate with the administrator to define and assign custom access perimeters to each resident of the facility. For example, the computer system can: assign a large, generic access perimeter around the facility to all residents; and assign smaller access perimeters within particular regions of the facility to select residents, such as based on each resident's mobility status, mental health or memory status, etc. In this example, the computer system can assign access perimeters restricted to floors or rooms within the facility, to grounds areas around the facility, etc. The computer system can also set time-dependent access perimeters to all or select residents, such as a daytime generic access perimeter around the full grounds of the facility for all residents and resident-specific nighttime access perimeters around the perimeters of the buildings in which the residents sleep.

In one implementation, the computer system can: calculate a perimeter risk for the resident based on a frequency of perimeter events noted in a set of previous electronic incident reports identifying the resident; and, in response to the perimeter risk of the resident exceeding a risk threshold, assigning a second access perimeter contained fully within the generic access perimeter to the resident. For example, for a particular resident who has triggered three perimeter breach events within the span of a single week, the computer system can assign to the resident a second access perimeter (e.g., an access perimeter offset inside the generic access perimeter by 20 feet)—fully contained within and smaller than a generic access perimeter assigned to other residents of the facility associated with lower perimeter risk scores—in order to trigger a breach event prompt at an earlier time as the resident moves toward a boundary of the facility (e.g., moves toward the generic access perimeter). The computer system can thus assign a second access perimeter of reduced size to a particular resident in order to enable care providers to reach the particular resident and to redirect the particular resident back into the facility following receipt of a perimeter response prompt, such as before the resident moves beyond a wireless range of wireless communication hubs interspersed throughout the facility, at which time the resident may no longer traceable through her wearable device.

The system can also dynamically adjust a generic or resident-specific access perimeter substantially in real-time during operation. For example, the computer system can scale a generic access perimeter: proportional to a number of care providers currently on duty within the facility; proportional to a number of care providers on duty and not currently occupied; or proportional to a number of care providers within 200 feet of the resident. However, the computer system can set an access perimeter for one or more residents of the facility in any other way.

7.2 Breach Event Location

Block S122 of the method S100 recites determining a location of a resident wearable device associated with the resident based on wireless communications between the resident wearable device and a set of wireless communication hubs within the facility. Generally, in Block S122, the computer system can implement methods and techniques described above in Block S112 to determine the location of a resident, such as an absolute geospatial location of the resident or a location relative to one or more wireless communication hubs or other wireless-enabled devices of known location within the facility.

In one implementation, the resident's wearable device broadcasts test signals once per five-second interval, receives response signals and UUIDs from local wireless communication hubs within the facility, and uploads these data to the computer system via a local wireless communication hub; the computer system then transforms these data into a location area or point of the resident's wearable device based on known geospatial positions of the wireless communication hubs recorded in a database or lookup table. The computer system can thus calculate a new location of the resident wearable device for each five-second interval, compare this location to the access perimeter assigned to the resident, and trigger a perimeter breach alarm if the resident's location area overlaps the access perimeter or if the resident's location point has moved outside of (or is inside but within a threshold distance of) an access perimeter assigned to the resident.

Alternatively, the resident's wearable device can automatically retrieve its geospatial location, such as once per interval, and transmit this location to the computer system. The computer system can then compare this geospatial location to the access perimeter assigned to the resident and trigger a perimeter breach alarm if the geospatial location point is outside of or is inside but within a threshold distance of the access perimeter.

In one implementation, the computer system can determine if a resident is approaching the access perimeter and trigger a perimeter breach alarm or distribute a perimeter response prompt accordingly. For example, the computer system can determine an initial location of a resident wearable device based on wireless communications between the resident wearable device and a set of wireless communication hubs, as described above; and, in response to the initial location of the resident wearable device falling within a threshold distance of the access perimeter, distribute a perimeter observation prompt indicating the initial location of the resident and including a prompt to observe the resident. For example, in response to a resident moving to within ten feet of her assigned access perimeter, the computer system can distribute a prompt to a set of mobile computing devices associated with a set of care providers prompting the care providers: to move to locations within the facility at which the care providers can observe the resident; and to confirm that the resident is not attempting to breach the perimeter, such as without contacting the resident or otherwise engaging with the resident directly. The perimeter observation prompt can thus prompt care providers to check on residents from afar as the resident nears her assigned access perimeter. In this example, the computer system can include the location of the resident in the prompt distributed to care providers. The computer system can also include the frequency of past perimeter breach events by the resident in this prompt in order to indicate a risk that the resident may leave the facility to these care providers.

In another implementation, in response to the initial location of the resident falling within a threshold distance of the access perimeter, the computer system can identify care providers within a threshold distance of the resident, such as within 200 feet (or other threshold distance) of the resident or otherwise in a position to respond quickly to the resident's trajectory out of the facility, and distribute a perimeter observation prompt to a set of computing devices associated only with care providers identified as located within the threshold distance of the resident. The computer system can also cross-reference locations of care provider computing devices with a map of the facility at the time that the location of the resident falls within the threshold distance of the access perimeter and then determine which care provider computing devices are within or almost within eyeshot of the resident (i.e., care providers with a direct visual path to the resident unobstructed by walls, floors, or other barriers) and distribute the perimeter observation prompt to these care provider wearable devices.

In a similar implementation, the computer system can trigger a perimeter breach alarm only if the location of the resident is outside of or is inside but within a threshold distance of the access perimeter for a threshold period of time (hereinafter a "breach threshold time"). For example, the computer system can trigger a perimeter breach alarm in response to the location of the resident falling outside of the access perimeter for a period of time exceeding 60 seconds. In another example, an administrator of the facility may indicate through an administrator portal that it is customary at the administrator's facility to allow residents to greet incoming visitors and to walk outgoing visitors outside of the facility (e.g., at a front door). In this example, the computer system can trigger a perimeter breach alarm only after the determining that the resident has been outside of the access perimeter for more than a breach threshold time, such as five minutes, accordingly.

The computer can additionally assign custom breach threshold times to each resident of the facility. For example, the care providers or managers at a facility may identify—within a care provider or manager portal hosted by the computer system—certain residents of the facility as "high-risk" for breach events, such as residents with Alzheimer's disease or residents with a propensity for violence. In this example, the computer system can automatically assign a null breach threshold time (i.e., a breach threshold time of zero seconds) to these high-risk residents while assigning other residents of the facility a breach threshold time of thirty seconds. In another example, the care providers or managers may identify residents of the facility with track records of good behavior ("low-risk" residents). The computer system can assign a breach threshold time of sixty seconds to these low-risk residents while assigning a null breach threshold time to other residents. The computer system can thereby improve the lives of low-risk residents or incentivize good behavior from other residents.

The computer system, the resident's wearable device, and/or other local devices can continue to track the location of the resident's wearable device following detection of a perimeter breach event, such as at the same or increased frequency. The computer system can then transmit resident location updates to care provider wearable devices or computing devices substantially in real-time—such as to all care providers in the facility or to a particular care provider who elected to respond to the corresponding perimeter response prompt—until a care provider reaches the resident.

However, in Block S122, the computer system can function in any other way to identify a perimeter breach event.

7.3 Perimeter Response Prompts

The computer system can similarly handle generation and distribution of perimeter response prompts to care providers within the facility. In particular, the computer system can execute one variation of Block S130 that recites, in response to the location of the resident wearable device falling outside of the access perimeter, distributing a perimeter response prompt to a set of computing devices within the facility, each computing device in the set of computing devices associated with a care provider, the perimeter response indicating the location.

Generally, the computer system can implement methods and techniques similar to those described above to aggregate perimeter breach data—such as including the last known or current location of the resident, the resident's name, a photograph of the resident, and a mental health status (e.g., diagnosed degree of dementia), etc.—into a perimeter response prompt. The computer system can then transmit instances of the perimeter response prompt to computing devices and/or care provider wearable devices associated with all or a subset of care providers currently on duty within the facility. For example, in response to a perimeter breach event, the computer system can implement methods and techniques similar to those described above to filter all care providers currently on duty to a subset of care providers who specialize in oral communications with residents, who are associated with positive resident collection results, or who have developed a relationship with the resident who breached his access perimeter.

In response to a perimeter breach event, the computer system can also identify and elect additional recipients of the perimeter response prompt outside of the facility. For example, in response to a perimeter breach event by a resident, the computer system can retrieve from a database contact data for a list of preferred contacts associated with the resident, such as a phone number or email address for each of a spouse or child. In response to a perimeter breach event, the computer system can communicate with computing devices affiliated with a preferred contact associated with the resident to identify contacts nearby (e.g., within a threshold distance, such as within one-quarter mile or within a five-minute walk, of) the resident. In the example, the computer system can then selectively transmit instances of the perimeter response prompt to computing devices associated with such contacts who are within the threshold distance of the resident.

However, the computer system can implement any other methods or techniques to generate a perimeter response prompt and/or to transmit the perimeter response prompt to care providers within the facility.

7.4 Perimeter Response Prompt Confirmation

The computer system can implement methods and techniques similar to those described above for fall events to prompt care provider to respond to perimeter breach events. Furthermore, as described above, after detecting a perimeter breach event, the computer system can consistently access (e.g., pull) location data (e.g., a GPS location) directly from the resident's wearable device, access test signal time of flight data from the resident's wearable device, or access wireless signal strength data from one or more wireless communication hubs near the resident's wearable device (nearest hub), etc. and convert these data into an approximate location of the resident, such as at a rate of once every five seconds between detection of the perimeter breach event and detected arrival of a care provider at or near the resident. The computer system can then transmit these updated resident location data to all recipients of the perimeter response prompt or to a particular care provider who elected to respond to the perimeter response prompt, such as at a similar rate of once every five seconds until a care provider reaches the resident.

8. Response Verification

One variation of the method S100 includes Block S180, which recites verifying arrival of the first care provider at the location of the resident based on establishment of a wireless connection between the first computing device of the first care provider and the resident wearable device worn by the resident. Generally, in Block S180, the computer system functions to confirm a care provider's presence near the resident following the care provider's election to respond to the fall response prompt (the "first care provider").

In one implementation, the computer system implements methods and techniques similar to those described above to determine and to track the location of the first care provider after the first care provider elects to response to the fall (or perimeter) response prompt. In one example, the computer system pulls GPS location data from a computing device or from a care provider wearable device assigned to the first care provider, such as at a rate of once every five seconds between receipt of the care provider's election to respond to the fall response prompt and determination that the care provider is at or near the resident. Once the first care provider is determined to be within a threshold distance of (e.g., less than five feet from) the resident, the computer system can confirm that the first care provider is responding to the fall event (or proximity event) and can automatically transmit an incident report to the first care provider in Block S150.

Alternatively, the computer system can determine that the first care provider has reached the resident based on (near)-physical contact made between the resident's wearable device and the first care provider's wearable device (or computing device, etc.). For example, upon reaching the resident, the first care provider can tap his wearable device against the resident's wearable device; both wearable devices can transmit accelerometer data, location-related data, or other relevant data to the computer system, and the computer system can match the impact events detected at each wearable device to determine that the first care provider's wearable device contacted the resident's wearable device, thereby confirming that the first care provider reached the resident.

In another implementation, the first care provider's wearable device (or computing device) can automatically wirelessly pair with the resident's wearable device, receive a UUID from the resident's wearable device, and transmit the UUID to the computer system (and/or vice versa); the computer system can pass the UUID received from the resident's into a lookup table to confirm that the first care provider's wearable device is communicating with (i.e., is within wireless range of) the resident's wearable device. The care provider's wearable device can then quantify the strength of wireless signals received from the resident's wearable device and pass these data to the computer system; the computer system can correlate these signal strength data with distances between the two wearable devices and confirm that the first care provider has reached the resident when a calculated distance between the wearable devices falls below a threshold distance.

However, the computer system, the resident and care provider wearable device, wireless communication hubs, and/or any other local device can cooperate to collect relevant data and to determine that the first care provider has reached the resident.

In one implementation, the computer system can track time elapsed between transmission of a fall response or perimeter response prompt and the response verification. For example, the computer system can: verify the arrival of a care provider at the location of the resident based on an establishment of a wireless connection between the computing device of the care provider and the resident wearable device worn by the resident; record a duration of time between distribution of the fall event prompt to the set of care provider computing devices and the arrival of a first care provider at the resident's location; and automatically write this duration to the electronic incident report for the fall event (and to the care provider's response history).

For access perimeter breach events, the computer system can continue to monitor the locations of the first care provider and/or the resident once the first care provider reaches the resident to determine when the resident has been returned to an access area bound by his assigned access perimeter. In this variation, the computer system can also record the location of the resident when met by the first care provider and the amount of time, distance traversed, and maximum, minimum, and/or average speed observed by the resident as the resident is guided back to his access area following the breach event; the computer system can automatically populate the incident report with such data in Block S160.

The computer system can similarly interface with the resident's wearable device, the recipient's wearable device, and/or the computing device to track a time from distribution of the fall response prompt to confirmed proximity of a care provider to the resident (e.g., a "bump" between the resident wearable device and the care provider wearable device, as described below). In one example, when a particular care provider submits a fall response confirmation in response to a fall response prompt, the system can set a timer, such as for a duration of 45 seconds; if a confirmation for proximity of the particular care provider's wearable device or computer system to the resident's wearable device is not received before the timer expires, the system can clear the fall response confirmation and transmit a second fall response prompt to care providers within the facility.

The computer system can also aggregate the foregoing duration data and other metadata with similar data recorded during previous fall events (and/or proximity events, etc.), insert these data into the electronic incident report as described below, and/or package these data into a compliance report for a facility administrator, an insurance agency, etc.

9. Incident Report

Block S150 of the method S100 recites, in response to a proximity confirmation indicating proximity of the first computing device to the resident wearable device, authorizing edit permissions for an incident report by a first care provider associated with the first computing device; and Block S160 of the method S100 recites disabling edit permissions for the incident report by a second care provider associated with the second computing device. Generally, in Blocks S150 and Block S160, the computer system functions to deliver a virtual incident report to a first care provider who responded to the fall (or perimeter) response event and to enable the first care provider solely to edit (i.e., complete) the incident report. The computer system can similarly serve a virtual incident report to a group of (e.g., two or three) care providers who responded to the fall or response prompt.

In one implementation, the computer system transmits the virtual incident report to the first care provider's wearable device when the first care provider reaches the resident. The native care provider application executing on the first care provider's computing device can automatically open the incident report and prompt the first care provider to complete the incident report. The native care provider application can also enable the first care provider to "snooze" the incident report, and the native care provider application can later issue reminders to the first care provider to complete the incident report, such as every two minutes after the incident report is snoozed or when locations of the resident's and the first care provider's wearable devices indicate that the first care provider is moving away from the resident.

The computer system can also enable other care providers within the facility to view the incident report. However, the computer system can withhold incident report edit permissions from these other care providers such that the incident report can only completed by the care provider(s) who responded to the fall or perimeter breach event.

9.1 Automatic Data Population

As described above, the computer system and/or the native care provider application can automatically populate fields within the incident report, such as the resident's name and location, the type of the response (e.g., fall, perimeter breach), the first care provider's name, response time data, etc. The native care provider application also enables the first care provider to complete other fields in the incident report through the computing device, such as the type, severity, and location of any injury(ies) sustained by the recipient during a fall event, whether emergency services were required, or the resident's willingness to return to the facility during a perimeter breach event. Upon completion, the native care provider application can upload the incident report to the computer system, and the computer system can store the completed incident report in an incident report database.

The computer system (or the native care provider application) can automatically populate the incident report with a virtual map representing a state of the facility at the time of the fall or perimeter event. For example, the computer system can populate a virtual map of the facility with positions of a set of computing devices—issued to care providers including the care provider who first responded to the fall event—and a set of resident wearable devices—issued to residents of the facility, including the fallen resident—at a time of the fall event; and then insert the virtual map into the electronic incident report. In this example, the computer system can identify other residents and care providers who were near the location of (e.g., within 50 feet of) the fallen resident at the time of the fall event, some of whom may have witnessed the fall event, based on locations of their associated computing devices and wearable devices and insert a list of names of these care providers and residents into the incident report or label the virtual map with names of these care providers and residents. In this example, the computer system can also access a native resident application executing on a computing device associated with a second resident determined to be in the vicinity of the fall event at the time of the fall event to prompt the second resident to confirm if he or she witnessed the fall event. The computer system can then indicate in the incident report whether the second resident was witness to the fall event. A care provider, supervisor, or administrator, etc. may later access the electronic incident report to identify these care providers and residents and then inquire with these care providers and residents when investigating the fall event.

In one implementation, the computer system can: track motion of a resident toward an access perimeter prior to the perimeter breach event; insert representation of this motion of the resident toward the access perimeter into a virtual map of the facility; and insert this virtual map into the electronic incident report. For example, a resident may have found an unknown exit from the facility or an exit previously considered unreachable by residents, such as a hole in a fence around the facility or a improperly locked restricted-access door. The computer system can thus generate a map of the facility including the resident's path before, up to, and following a perimeter breach event in order to enable care providers or managers of the facility to identify these unknown exits indicated by the resident's path prior, up to, and following the perimeter breach event. In particular, the path of the resident prior to a perimeter breach event may indicate a common escape route, which a care provider or manager of the facility can then preempt by closing the unknown exit. Similarly, the computer system can implement machine learning techniques to automatically identify these unknown exits and to adjust a generic access perimeter or custom access perimeters for residents of the facility in order to identify and rapidly respond to a perimeter breach event when a resident nears or reaches such unknown exits.

9.2 Resident Confirmation

One variation of the method S100 includes Block S170 which recites retrieving occupant identification data associated with the unique identifier of the occupant wearable device; inserting the occupant identification data into the electronic incident report; at the computing device, prompting the first care provider to confirm that the occupant identification data corresponds to the occupant; and, in response to entry of alternate occupant identification data into the electronic incident report, re-associating the unique identifier of the occupant wearable device with the alternate occupant identification data. Generally, in Block S170, the computer system (the native care provider application) functions to confirm that the unique identifier associated with the resident wearable device is correctly associated with the fallen resident.

In one implementation, the native care provider application: receives a unique identifier associated with the resident wearable device worn by the fallen resident; retrieves, from the computer system, resident identification data of the resident associated with the unique identifier, such as the resident's name, age, and gender; and automatically populates the incident report with the resident identification data. The native care provider application can then prompt the care provider to confirm that the resident identification data pulled from the computer system matches the fallen resident. In response to an indication from the care provider that the identification data does not match the fallen resident, the computer system can re-associate the unique identifier associated with the resident wearable device with the correct resident. The computer system and the native care provider application can cooperate to confirm an association between a resident wearable device and a resident or correctly re-affiliate a resident wearable device with a resident—such as if resident wearable devices are disordered among residents of the facility—with each fall or perimeter event.

However, the computer system can cooperate with an instance of the native care provider application in any other way to serve, complete, and store virtual incident reports to care providers responding to fall and/or perimeter breach events.

10. Fall Detection Model

One variation of the method S100 includes Block S112, which recites retraining the enlarged form of the abbreviated fall detection model based on the output of the motion sensor, the output of the pressure sensor, and corroboration of the fall event. Generally, in Block S112, the computer system functions to update the fall detection model with subsequently recorded data. In the implementation described above in which the resident wearable device and/or computer system execute a fall detection model (e.g., a compressed fall detection model and a complete fall detection model, respectively), the computer system can retrain the fall detection model based on data extracted from a completed incident report. In one implementation, in response to completion of an electronic incident report by a care provider, the computer system can corroborate the fall event from data (e.g., confirmation of the fall event) stored in the electronic incident report; label motion and pressure data—output by and pressure sensors integrated into the wearable device—recorded during the fall event as positively corresponding to a fall event; retrain the complete fall detection model based on these motion data, these pressure data, and the positive fall event label; generate a new compressed fall detection model based on the complete fall detection model; and upload the new compressed fall detection model to the resident's wearable device.

The computer system can also retrain the fall detection model based on positive and negative confirmations of fall events. For example, when a resident cancels a fall response prompt at her wearable device to confirm that the she did not fall, the computer system can label the corresponding fall event as a false positive fall event and retrain the complete fall detection model accordingly. The computer can then generate a new compressed fall detection model based on the new complete fall detection model and upload the new compressed fall detection model to the resident's wearable device (and to all other deployed wearable devices).

However, the computer system can retrain the fall detection model based on any other sensor data and feedback collected by a resident wearable device, a care provider wearable device, and/or a resident or care provider over time.

11. Specialist Care

One variation of the method S100 includes Block S190, which recites predicting a type of specialist care needed by the resident based on data contained in the electronic incident report. Generally, in Block S190, the computer system functions to alert a care specialist that a resident may be in need of specialist care, and to serve the resident to the care specialist. In one implementation, in response to completion of the incident report (e.g., by the first care provider at the first computing device), the computer system uploads the incident report to an incident report database, generates a specialist care prompt based on data contained in the incident report, and distributes the specialist care prompt to a care specialist associated with the type of the specialist care prompt.

For example, if the first care provider indicates on the incident report that the resident impacted a right knee on the floor upon falling, the computer system can automatically generate a prompt including the resident's name and a request to inspect the resident's right knee and can then transmit this prompt to a resident physician or to an orthopedic surgeon. In this example, the computer system can automatically draft an email, a textual notification (e.g., SMS), a message within an assisted living management system, or any other suitable type of communication including these data and transmit this communication to an electronic address or profile affiliated with the doctor or surgeon. In this example, the computer system can additionally or alternatively generate a prompt including the resident's name and a request to administer an anti-inflammatory medication to the resident and can then transmit this prompt to a pharmacist or nurse on staff at the facility.

The computer system can also distribute a specialist care prompt based on the medical history of a resident. In one implementation, the computer system can determine a type of specialist care needed by the resident based on the magnitude of the resident's fall and the medical history of the resident. For example, the resident's wearable device can calculate or estimate a magnitude of the resident's fall based on outputs of an accelerometer integrated into the wearable device during the fall event, such as proportional to a peak acceleration during the fall event, and then return this fall magnitude to the computer system via a local wireless communication hub. (Alternatively, the computer system can calculate a magnitude of the fall based on raw acceleration data received from the resident's wearable device, such as with the fall event notification.) The computer system can then: associate the fall event magnitude with a type of specialist care needed by the resident based on a medical history of the resident. For example, the computer system can: access the resident's medical records to determine that the resident has a history of back surgeries, a back injury, or experiences back pain; and then predict that the resident will require a spine specialist after determining that the magnitude of the resident's fall exceeded a preset threshold magnitude for resident's with back injuries. The computer system can then prompt a spine specialist to view the resident by transmitting an electronic communication (e.g., an email) to an account associated with the spine specialist (e.g., the specialist's email account). The computer system can additionally automatically note in an incident report that the spine specialist was contacted. Similarly, the computer system can serve a prompt to a nurse, administrator, assistant, or other care provider of the facility to schedule an appointment between the resident and the spine specialist in response to such predicted need of the resident following the fall event.

Alternatively or additionally, the computer system can predict a type of specialist care needed by the resident based on data written to the incident report, such as by the respondent care provider. The computer system can, in response to completion of an electronic incident report by the respondent care provider, upload the electronic incident report to an electronic incident report database; predict a type of specialist care needed by the resident based on data contained in the electronic incident report; and transmit a specialist care prompt to serve the resident to a care specialist associated with the type of specialist care. For example, the respondent care provider may take the resident's blood pressure when responding to the fall event and write this blood pressure value to the electronic incident report. The computer system can later determine that the resident exhibited very high blood pressure at the time of the fall event based on data contained in the electronic incident report. In this example, the computer system can predict that the resident has suffered a stroke and then distribute a specialist care prompt to a stroke specialist or neurologist accordingly.

14. Event Metrics

Figure 8:
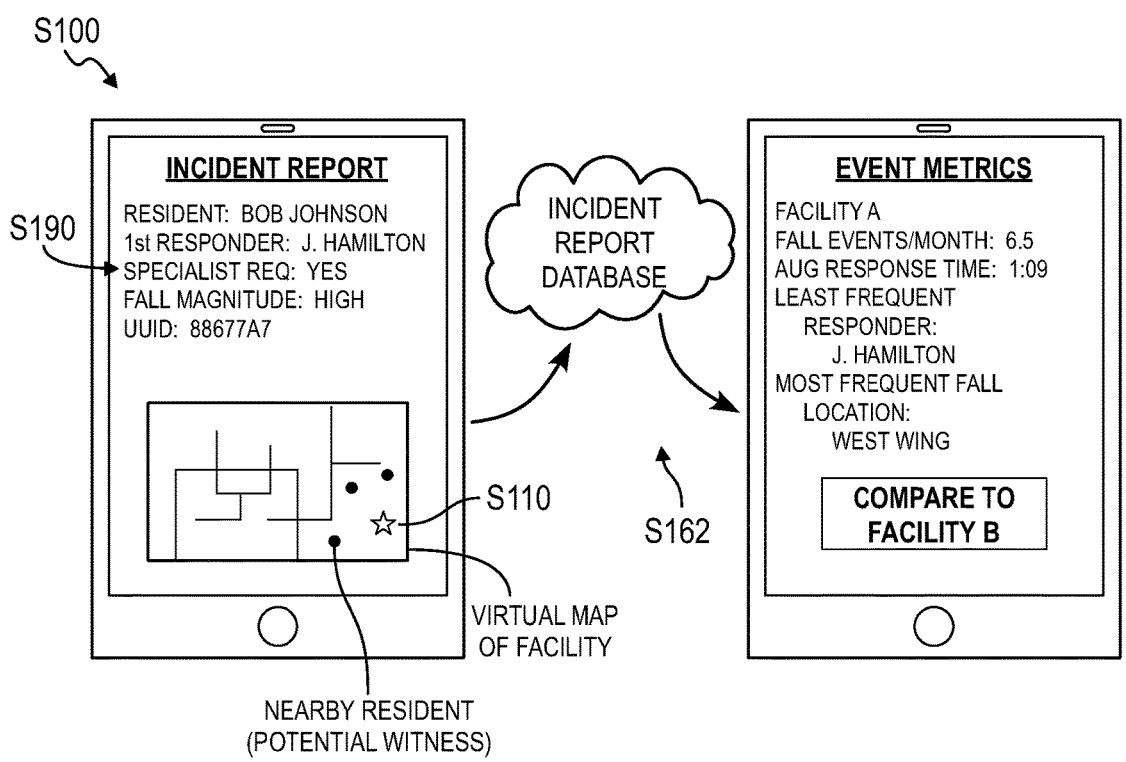
FIG. 8 is a flowchart representation of one variation of the method.

One variation of the method S100 includes Block S162. Generally, in Block S162, the computer system functions to extract trends from the data stored in the incident report database, as shown in FIG. 8. As described above, the computer system can generate and facilitate the completion of incident reports by care providers at a care providing facility. The computer system can also extrapolate trends from incident reports generated over time and track and analyze metrics associated with these incident reports.

The computer system can analyze incident reports stored in an incident report database to determine any number of trends regarding the fall (or perimeter) events. For example, the computer system can identify residents who fall most frequently and then prompt care providers to remain in closer proximity to this resident in order to be more readily available to stop these resident from falling or to help these residents more rapidly when they do fall. In another example, the computer system can: identify specific care providers who respond to fall events most frequently and with the greatest speed; identify other care providers who do not respond to fall event prompts; and calculate an average response time for fall events at the facility or during particular hours, days, or shifts at the facility. In this example, the computer system can thus prompt an administrator of the facility to reward select care providers, admonish other care providers, and/or add care providers to certain shifts in order to reduce response time. In another example, the computer system can identify locations within the facility at which fall events most frequently occur, which may indicate dangerous locations within the facility, and then prompt a facility administrator to observe or modify these locations accordingly.

In one implementation, the computer system: accesses past incident reports from an incident report database; calculates a frequency of fall events occurring within proximity of a particular resident at the facility based on virtual maps of the facility and its residents recorded in incident reports generated over time; and prompts care providers at the facility to increase their observation of the particular resident if the frequency of fall events occurring within proximity of the particular resident exceeds a threshold frequency. In particular, the computer system can extrapolate a trend in fall events occurring near a particular resident and prompt care providers of the facility to observe this particular resident more closely if the particular resident is near a frequency of falls significantly greater than average. For example, the computer system can determine that the same 70-year-old male resident has been in the vicinity of a high number of fall events and that the resident should be placed under increased surveillance based on locations of residents of the facility recorded in virtual maps written to incident reports generated at the facility over time.

In another implementation, the computer system can store incident reports from multiple facilities in a common incident report database. In this implementation, the computer system can identify trends common to these facilities or compare the performance of one facility to that of another. For example, the computer system can calculate an average fall event response time of two minutes for Facility A and an average fall event response time of five minutes for Facility B. In this example, after identifying a discrepancy in fall event response time between these two facilities, the computer system can notify a manager affiliated with both facilities of this discrepancy and prompt the manager to review Facility B's fall event response procedures.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated within apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for detecting and handling events in a facility, the method comprising:
   at a first time, detecting an intervention event based on data received from a resident wearable device associated with a resident of a facility;
   calculating a location of the resident wearable device within a facility at approximately the first time;
   in response to detecting the intervention event, distributing an event prompt to a set of computing devices within the facility, each computing device in the set of computing devices associated with a care provider, the event prompt indicating the location; and
   in response to receipt of an event confirmation from a first computing device within the set of computing devices, deescalating the event prompt at a second computing device within the set of computing devices.

2. The method of claim 1, further comprising, in response to confirmation that the first computing device is proximal the resident wearable device, authorizing edit permissions for an electronic incident report by a first care provider associated with the first computing device exclusive of a second care provider associated with the second computing device.

3. The method of claim 1, wherein deescalating the event prompt at the second computing device comprises, in response to receipt of the event confirmation from a first care provider via the first computing device:
   silencing the event prompt at the second computing device; and
   transmitting an indicator of response to the intervention event by the first care provider to the second computing device.

4. The method of claim 1, further comprising, in response to absence of an event confirmation from a computing device within the set of computing devices within a threshold period of time following distribution of the event prompt to the set of computing devices, distributing a second event prompt to a second set of computing devices comprising a third computing device associated with a supervisor of the facility.

5. The method of claim 4, further comprising, in response to absence of an event confirmation from a computing device within the second set of computing devices within a second threshold period of time following distribution of the second event prompt to the second set of computing devices, transmitting an alarm to an external emergency responder.

6. The method of claim 1, wherein:
distributing the event prompt to the set of computing devices within the facility, each computing device in the set of computing devices associated with a care provider, the event prompt indicating the location, further comprises:
  for each computing device in the set of computing devices, requesting activity data from the computing device;
  selecting a set of inactive computing devices from the set of computing devices, the set of inactive computing devices characterized by low-intensity activity data; and
  distributing the event prompt to the set of inactive computing devices; and
in response to receipt of an event confirmation from the first computing device within the set of computing devices, deescalating the event prompt at a second computing device within the set of computing devices further comprises, in response to receipt of an event confirmation from a first computing device within the set of inactive computing devices, deescalating the event prompt at a second computing device within the set of inactive computing devices.

* * * * *